United States Patent
Srivastava et al.

(10) Patent No.: US 11,112,950 B2
(45) Date of Patent: Sep. 7, 2021

(54) PERSONALIZING APPLICATION INTERFACES BASED ON USAGE

(71) Applicant: Conduent Business Services, LLC, Dallas, TX (US)

(72) Inventors: Saurabh Srivastava, Bangalore (IN); Simarjot Kaur, Bangalore (IN); Tuhin Bhattacharya, West Bengal (IN); Nupur Labh, Bangalore (IN); James Macurak, Glendale, AZ (US); Anuj Mahajan, M. P. (IN); Arun Rajkumar, Chennai (IN); Satish Prasad Rath, Bangalore (IN); Narayanan Unny, Karnataka (IN)

(73) Assignee: Conduent Business Services, LLC, Florham Park, NJ (US)

(*) Notice: Subject to any disclaimer, the term of this patent is extended or adjusted under 35 U.S.C. 154(b) by 256 days.

(21) Appl. No.: 15/986,161

(22) Filed: May 22, 2018

(65) Prior Publication Data

US 2019/0361579 A1 Nov. 28, 2019

(51) Int. Cl.
| | | |
|---|---|---|
| *G06F 3/0484* | (2013.01) | |
| *G06F 3/0482* | (2013.01) | |
| *G06F 3/0481* | (2013.01) | |
| *A61B 5/00* | (2006.01) | |

(52) U.S. Cl.
CPC ........ *G06F 3/0484* (2013.01); *A61B 5/0002* (2013.01); *A61B 5/746* (2013.01); *A61B 5/7435* (2013.01); *A61B 5/7475* (2013.01); *G06F 3/0482* (2013.01); *G06F 3/04817* (2013.01); *A61B 2560/0223* (2013.01)

(58) Field of Classification Search
CPC .... G06F 16/2428; G06F 16/38; G06F 16/387; G06F 16/435; G06F 16/436; G06F 16/80; G06F 3/048; G06F 40/00; G06F 3/0484; G06F 3/0482; G06F 3/04817; G06F 9/4451; G06F 3/04886; G06F 9/451; G06N 5/00; G06N 20/00; G06N 20/20; A61B 5/7435; A61B 5/7475; A61B 5/0002; A61B 2560/0223
See application file for complete search history.

(56) References Cited

U.S. PATENT DOCUMENTS

| | | | |
|---|---|---|---|
| 5,596,994 A | 1/1997 | Bro | |
| 8,793,569 B2 | 7/2014 | Hoshino | |
| 9,729,403 B1 * | 8/2017 | Rabe | G06F 3/04895 |
| 2007/0106628 A1 | 5/2007 | Adjali et al. | |
| 2013/0024464 A1 | 1/2013 | Berner et al. | |
| 2014/0278264 A1 | 9/2014 | Bukhin et al. | |

(Continued)

FOREIGN PATENT DOCUMENTS

| | | |
|---|---|---|
| CA | 2 860 288 A1 | 2/2015 |
| CN | 105 138 508 A | 12/2015 |
| WO | 2006/107032 A1 | 10/2006 |

*Primary Examiner* — Sanchita Roy
(74) *Attorney, Agent, or Firm* — Jones Robb, PLLC

(57) ABSTRACT

System and methods for personalizing an application include an application server for hosting an application that is executed on a wireless device, the server being configured to monitor usage of a user interface including an interaction between a user of the application and one or more user interface elements and present an updated user interface comprising one or more additional user-interface elements based on the usage.

16 Claims, 8 Drawing Sheets

(56) References Cited

U.S. PATENT DOCUMENTS

| | | | | |
|---|---|---|---|---|
| 2014/0359472 A1* | 12/2014 | Lefor | .................... | G06F 3/0481 |
| | | | | 715/746 |
| 2015/0119668 A1* | 4/2015 | Mayou | ................... | G16H 40/63 |
| | | | | 600/365 |
| 2015/0339004 A1* | 11/2015 | Haydn | .................... | G06F 9/451 |
| | | | | 715/825 |
| 2017/0024546 A1 | 1/2017 | Schmidt | | |
| 2017/0212650 A1* | 7/2017 | Sinyagin | ............... | G06F 3/0484 |
| 2018/0364879 A1* | 12/2018 | Adam | ................... | G06F 3/0484 |

* cited by examiner

PERSONALIZING APPLICATION INTERFACES BASED ON USAGE

TECHNICAL BACKGROUND

There are ongoing challenges associated with the growth and evolution of wireless devices and networks. For example, increasing numbers of users are performing tasks on their wireless devices that were previously being performed on computers, or that were not being performed at all (such as real-time communication, technical support, content generation and management, etc.). Many tasks and/or services are accessed by a user via applications on their wireless devices. Advances in network technology have enabled real-time provisioning and/or configuring of such applications, for example by a network node or application server that hosts the application. Loading an application on a wireless device can include providing an interface with which the user may interact, such as a graphical user interface (GUI).

Challenges arise when different users interact with the same application in a different manner. For example, a first user accessing a service via an application on a wireless device may provide different inputs, understand prompts differently, or utilize the application more or less frequently than a second user. Consequently, providing both first and second users with the identical user interface or prompts/questions may result in inefficient utilization of the application. For example, prompts that are not properly understood by certain users may end up wasting network resources as well as cause the users to access alternative means for performing the task or accessing the service. In other words, prompts and recommendations that are pushed to wireless devices and remain unanswered create additional network overhead in terms of bandwidth and storage, owing to said prompts and recommendations remaining stagnant on the wireless device, or to the application server having to repeatedly transmit the same prompts and recommendations to the same wireless devices. Thus, the user base of an application may decline due to lack of effectiveness of the application. For example, inefficient usage of computing and network resources typically caused by, for example, poor communication between applications and users, limited usage of applications, abandoned/inactive user accounts, etc. In another example, a health service provider may require patients at home to provide updates related to their health status using a proprietary application. If the prompts or recommendations delivered to the user's wireless device are not effective or persuasive, then the user may ignore the prompts and recommendations, and their health may decline.

OVERVIEW

Exemplary embodiments described herein include systems and methods for personalizing an application, the system comprising an application server for hosting an application, a wireless device for executing the application hosted on the application server, and a processor coupled to the application server. The processor is configured to perform operations comprising transmitting a first plurality of prompts to the wireless device via the application, monitoring a usage of the application, wherein the monitoring comprises monitoring responses to the first plurality of prompts, determining, based on the usage, one or more additional prompts, and transmitting the one or more additional prompts to the wireless device.

Monitoring the usage of the application further comprises determining that there are no responses to the first plurality of prompts. Monitoring the usage of the application further comprises monitoring a time or frequency of responses to the one or more prompts. The operations further comprise classifying a user of the wireless device based on the responses to the first plurality of prompts. The one or more additional prompts are determined based on the classification of the user. The one or more additional prompts are selected from a library comprising a plurality of additional prompts. Classifying the user may be performed using a machine learning algorithm.

The operations further comprise: receiving sensor data from one or more of the plurality of sensors; and determining the one or more additional prompts based on a combination of the usage data and the sensor data. The operations further comprise transmitting commands to at least one of the plurality of sensors based on the sensor data and the usage of the application. The commands may comprise a calibration command to calibrate the at least one sensor. The commands may further comprise a measurement command to the at least one sensor to perform a measurement. The plurality of sensors may comprise health sensors.

DETAILED DESCRIPTION

Systems and methods described herein for personalizing an application are configured to transmit a first user interface to a wireless device via the application, monitor a usage of the first user interface, determining a modification to the first user interface based on the usage, and transmitting a second user interface to the wireless device, the second user interface including the modification to the first user interface. The modified user interface displayed on the wireless device is therefore personalized based on a user's interaction with the application, which results in optimized user interaction or engagement with the application. This further minimizes inefficient usage of computing and network resources typically caused by, for example, poor communication between applications and users, limited usage of applications, abandoned/inactive user accounts, etc.

Figure 1:
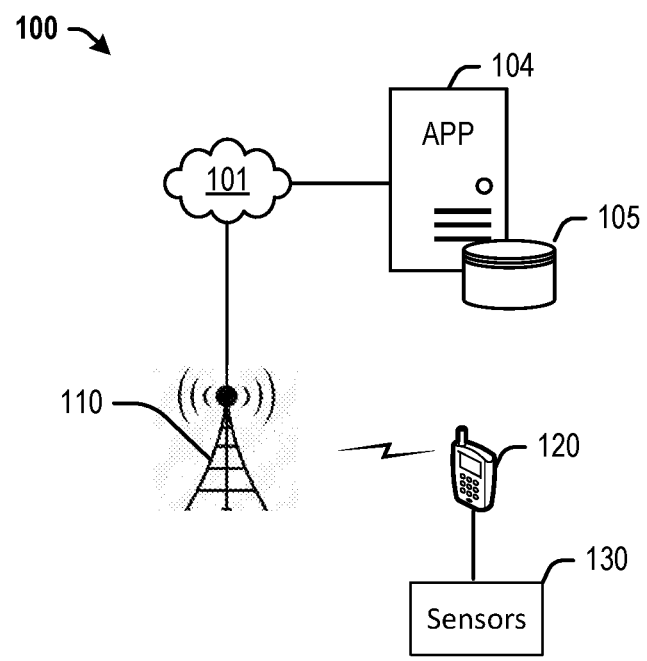
FIG. 1 depicts an exemplary system for personalizing applications based on usage.

FIG. 1. illustrates an exemplary system 100 for personalizing an application based on a usage of the application. System 100 comprises a network 101, an application server 104 coupled to network 101 for hosting an application, a wireless device 120 for executing the application hosted on the application server, and an access node 110 for enabling communication between wireless device 120 and network 101. Application server 104 may further comprise a storage 105 for storing instructions that are executed by application server 104 (using, for example, a processor not shown herein) to perform operations comprising transmitting a first user interface element to wireless device 120 via the application, monitoring a usage of the first user interface element, wherein the monitoring comprises monitoring an interaction between a user of the application and the first user interface element, determining, based on the usage, one or more additional user-interface elements, and transmitting the one or more additional user-interface elements to wireless device 120.

For example, a user of wireless device 120 may be classified into one or more stages based on the interaction with the application. Identifying one or more stages in which the user may be classified may be based, in part, on the usage of the application. The one or more stages may be related to a proficiency level, an interest level, a behavioral level, or any other classification based on the type of application or the requirements of an operator of application server 104. Each level may comprise a value on a scale from a minimum value to a maximum value. For example, a proficiency level may comprise a number between 0 and 10, with a proficiency level of 0 being associated with a user who is completely new to using applications on electronic devices (such as, for example, a senior), and a proficiency level of 10 being associated with an expert, such as an application interface designer. In another example, a behavioral level may be based on a model of behavioral change, and may include stages such as a contemplation stage, a preparation stage, an action stage, a maintenance stage, and a relapse stage. These and other stages are detailed with reference to the embodiments further described herein. Further, classifying the user, or identifying a stage of the user, may be performed using a machine learning algorithm stored on storage 105. As further described below, the machine learning algorithm may be trained for a period of time, either by the operator of application server 104 using, for example, a training set, or by monitoring the usage of the application by the user of wireless device 120 for a specified time period or usage threshold.

The one or more additional user-interface elements may be determined based on the classification of the user. For example, as the stages are arranged in a hierarchical order of levels, the one or more additional user-interface elements may also be grouped in a corresponding hierarchical order. The additional user-interface elements (along with the previous user interface element) may be selected from a library comprising a plurality of user-interface elements. Further, a trained machine learning algorithm may be used to select the additional user-interface elements based on a combination of the classification of the user and/or the interaction with the application. In an exemplary embodiment, in additional to the training stage of the machine learning algorithm, the selection or determination of the additional user-interface elements by the machine learning algorithm may be invoked upon a total number of inputs meeting a threshold. The machine learning algorithm may be stored on, for example, storage 105.

In further exemplary embodiments, system 100 includes a sensor 130 coupled to wireless device 120. For example, sensor 130 may comprise a medical device. Thus, operations performed by application server 104 (based on, for example, program instructions stored on storage 105) further include receiving sensor data from sensor 130, and determining the one or more additional user-interface elements based on a combination of the usage data and the sensor data. Commands may be transmitted to sensor 130 based on the sensor data and the usage of the application executing or being executed on wireless device 120. The commands may comprise a calibration command to calibrate sensor 120, or a measurement command to sensor 120 to perform a measurement.

Application server 104 may comprise any computing device capable of performing the operations described above and throughout this disclosure, under the control of a processing system executing computer-readable codes embodied on a computer-readable recording medium, such as data store 105. Access node 110 can comprise a processor and associated circuitry to execute or direct the execution of computer-readable instructions. For example, access node 110 can retrieve and execute software from data store 105, which can include a disk drive, a flash drive, memory circuitry, or some other memory device, and which can be local or remotely accessible. The software comprises computer programs, firmware, or some other form of machine-readable instructions, and may include an operating system, utilities, drivers, network interfaces, applications, or some other type of software, including combinations thereof. Further, access node 110 can receive instructions and other input at a user interface. Data store 105 may comprise any data storage device that can store data readable by a processing system, and includes both volatile and nonvolatile media, removable and non-removable media, and contemplates media readable by a database, a computer, and various other network devices. Data store 105 may comprise, for instance, read-only memory (ROM), random-access memory (RAM), erasable electrically programmable ROM (EEPROM), flash memory or other memory technology, holographic media or other optical disc storage, magnetic storage including magnetic tape and magnetic disk, and solid state storage devices. Data store 105 can also be distributed over network-coupled computer systems so that the computer-readable code is stored and executed in a distributed fashion. The communication signals transmitted through a transitory medium may include, for example, modulated signals transmitted through wired or wireless transmission paths.

Communication network 101 can be a wired and/or wireless communication network, and can comprise processing nodes, routers, gateways, and physical and/or wireless data links for carrying data among various network elements, including combinations thereof, and can include a local area network a wide area network, and an internetwork (including the Internet). Communication network 101 can be capable of carrying data, for example, to support voice, push-to-talk, broadcast video, and data communications by wireless devices 140, 150. Wireless network protocols can comprise MBMS, code division multiple access (CDMA) 1×RTT, Global System for Mobile communications (GSM), Universal Mobile Telecommunications System (UMTS), High-Speed Packet Access (HSPA), Evolution Data Optimized (EV-DO), EV-DO rev. A, Third Generation Partnership Project Long Term Evolution (3GPP LTE), and Worldwide Interoperability for Microwave Access (WiMAX). Wired network protocols that may be utilized by communication network 101 comprise Ethernet, Fast Ethernet, Gigabit Ethernet, Local Talk (such as Carrier Sense Multiple Access with Collision Avoidance), Token Ring, Fiber Distributed Data Interface (FDDI), and Asynchronous Transfer Mode (ATM). Communication network 101 can also comprise additional base stations, controller nodes, telephony switches, internet routers, network gateways, computer systems, communication links, or some other type of communication equipment, and combinations thereof.

Access node 110 can be any network node configured to provide communication between wireless device 120 and communication network 101, including standard access nodes such as a macro-cell access node, base transceiver station, a radio base station, an eNodeB device, an enhanced eNodeB device, or the like. Similar to application server 104, access node 110 can comprise a processor and associated circuitry to execute or direct the execution of computer-readable instructions, including communicating with application server 104 via network 101. Access node 110 can use various communication media, such as air, space, metal, optical fiber, or some other signal propagation path—including combinations thereof. For example, communications between access node 110 and one or both of network 101 and wireless device 120 can be wired or wireless and use various communication protocols such as Internet, Internet protocol (IP), local-area network (LAN), optical networking, hybrid fiber coax (HFC), telephony, Ti, or some other communication format—including combinations, improvements, or variations thereof. Other network elements may be present in system 100 to facilitate communication but are omitted for clarity, such as base stations, base station controllers, mobile switching centers, dispatch application processors, and location registers such as a home location register or visitor location register. Furthermore, other network elements that are omitted for clarity may be present to facilitate communication, such as additional processing nodes, routers, gateways, and physical and/or wireless data links for carrying data among the various network elements, e.g. between access node 110 and communication network 101.

Wireless device 120 may be any device, system, combination of devices, or other such communication platform capable of communicating wirelessly with access node 110 using one or more wireless frequency bands deployed therefrom. Wireless device 120 may be, for example, a mobile phone, a wireless phone, a wireless modem, a personal digital assistant (PDA), a voice over internet protocol (VoIP) phone, a voice over packet (VOP) phone, or a soft phone, as well as other types of devices or systems that can send and receive audio or data. Other types of communication platforms are possible.

Further, the methods, systems, devices, networks, access nodes, and equipment described herein may be implemented with, contain, or be executed by one or more computer systems and/or processing nodes. The methods described herein may also be stored on a non-transitory computer readable medium. Many of the elements of system 100 may be, comprise, or include computers systems and/or processing nodes. This includes, but is not limited to application server 104, access node 110, wireless device 120, and sensor 130.

Figure 2:
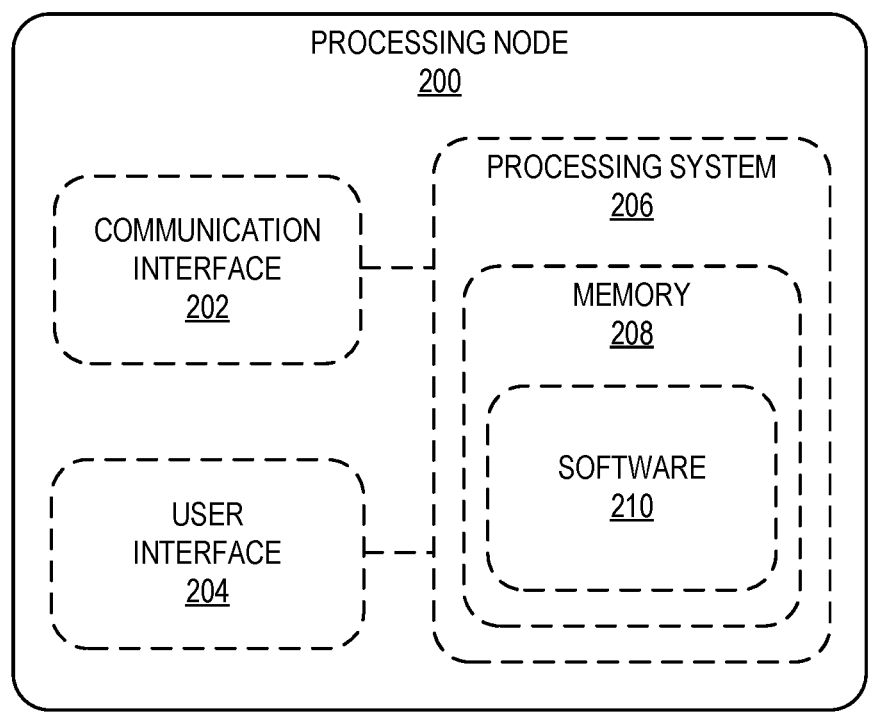
FIG. 2 depicts an exemplary processing node.

FIG. 2 depicts an exemplary processing node for scheduling resources for relay access nodes in a wireless network. Processing node 200 comprises a communication interface 202, user interface 204, and processing system 206 in communication with communication interface 202 and user interface 204. Processing system 206 includes storage 208, which can comprise a disk drive, flash drive, memory circuitry, or other memory device. Storage 208 can store software 210 which is used in the operation of the processing node 200. Storage 208 may include a disk drive, flash drive, data storage circuitry, or some other memory apparatus. For example, storage 208 may include a buffer. Software 210 may include computer programs, firmware, or some other form of machine-readable instructions, including an operating system, utilities, drivers, network interfaces, applications, or some other type of software. For example, software 210 may include a module for performing transmission power control operations described herein. Processing system 206 may include a microprocessor and other circuitry to retrieve and execute software 210 from storage 208. Processing node 200 may further include other components such as a power management unit, a control interface unit, etc., which are omitted for clarity. Communication interface 202 permits processing node 200 to communicate with other network elements. User interface 204 permits the configuration and control of the operation of processing node 200.

Figure 3:
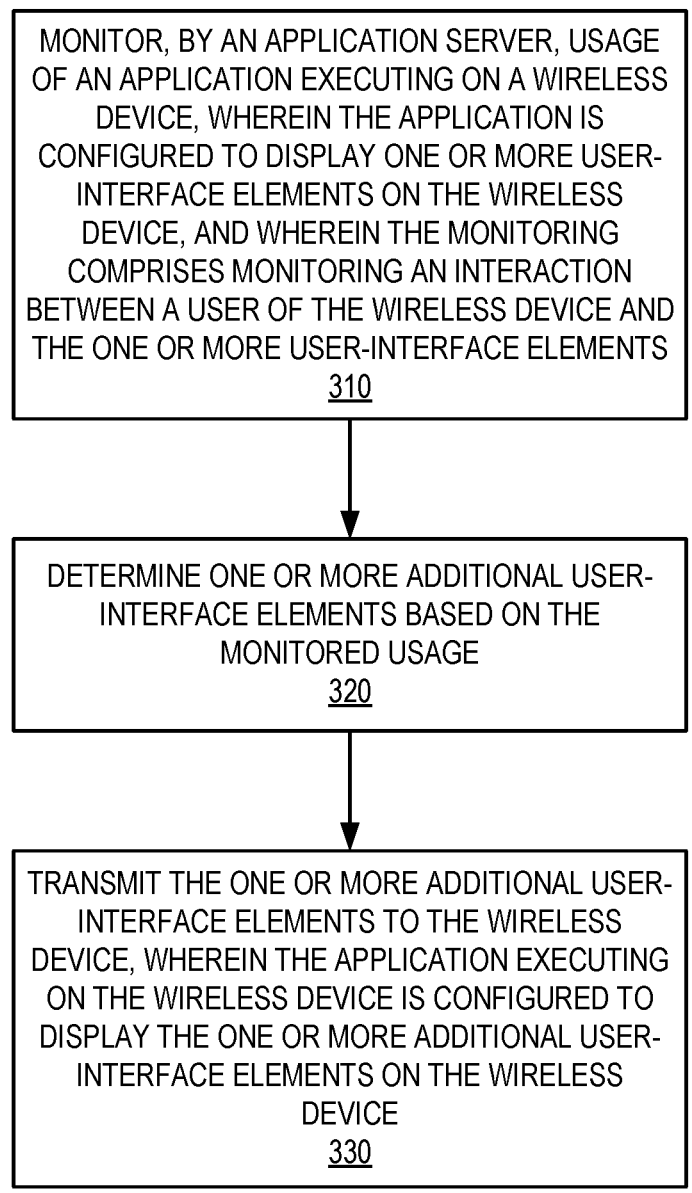
FIG. 3 depicts an exemplary method for personalizing applications based on usage.

FIG. 3 depicts an exemplary method for personalizing applications based on usage. The exemplary method of FIG. 3 may be implemented using components similar to those depicted in system 100, such as application server 104. Although FIG. 3 depicts steps performed in a particular order for purposes of illustration and discussion, the operations discussed herein are not limited to any particular order or arrangement. One skilled in the art, using the disclosures provided herein, will appreciate that various features described herein can be omitted, rearranged, combined, and/or adapted in various ways.

At 310, a usage is monitored of an application hosted on an application server and executing on a wireless device. For example, the application server is configured to display, on the wireless device via the application, one or more user-interface elements with which a user of the wireless device can interact. Thus, the monitoring comprises monitoring an interaction between the user of the application and the one or more user-interface elements. For example, the first user interface element comprises a prompt for an input. Monitoring the usage of the application therefore comprises one or more of detecting a first input to the prompt, measuring a time of the first input, measuring a length of the first input, determining a type of the first input, determining a frequency of responses to the prompt, or determining that there is no input. The type of first input may comprise one or more of a keypress, a button, an alphanumeric string, or a selection from a list.

Based on the monitored interaction, at 320, one or more additional user-interface elements may be determined. The user may be classified into one or more stages based on the interaction. Thus, the operations may further comprise identifying one or more stages in which the user may be classified based, in part, on the usage of the application. The one or more stages may be related to a proficiency level, an interest level, a behavioral level, or any other classification based on the type of application or the requirements of an operator of the application server. Each level may comprise a value on a scale from a minimum value to a maximum value. For example, a behavioral level may be based on a model of behavioral change, and may include stages such as a contemplation stage, a preparation stage, an action stage, a maintenance stage, and a relapse stage. In this example, a first behavior may be determined based on an initial interaction of the application. The initial interaction is programmed by the creator of the application, and includes a survey of questions for the user of the application. Based on the user input during the initial interaction, a preliminary determination may be made of a user's stage (or any other type of category). The preliminary determination, and subsequent classifications may be performed by a machine learning algorithm. Generally, the machine learning algorithm may be trained for a period of time, either by the operator of the application server, or by monitoring the usage of the application for a specified time period or usage threshold.

Thus at 320, the one or more additional user-interface elements may be determined based on the classification of the user. For example, as the stages are arranged in a hierarchical order of levels, the one or more additional user-interface elements may also be grouped in a corresponding hierarchical order. The additional user-interface elements (along with the previous user interface element) may be selected from a library comprising a plurality of user-interface elements. Further, a trained machine learning algorithm may be used to select the additional user-interface elements based on a combination of the classification of the user and/or the interaction with the application. In an exemplary embodiment, in addition to the training stage of the machine learning algorithm, the selection or determination of the additional user-interface elements by the machine learning algorithm may be invoked upon a total number of inputs meeting a threshold.

At 330, the one or more additional user-interface elements are transmitted to the wireless device, enabling the application to display the one or more user-interface elements on a user interface presented on the wireless device. In other words, an updated interface comprising any combination of user-interface elements as determined in step 320 may be displayed in step 330. The updated interface is customized to the user of the wireless device, enabling the user to more effectively interact with the user-interface elements presented thereon. Further, this method may be performed iteratively and in real-time, such that as the interaction or usage of the application changes over time, user interfaces are dynamically modified via real-time updating of user-interface elements. For example, the user may need to be re-classified based on different usage or patterns of interaction with additional user-interface elements. Thus, additional training, learning, monitoring, and/or classification operations may be performed at various frequencies, or in real-time. An optimal frequency may be determined based on a balance of user interface modifications and network resources. Results may be monitored in the form of changing behavior or interaction patterns, and poor or negative results may be caused by an infrequency monitoring. In one exemplary embodiment, a health monitoring and/or recommendation providing application may determine that a user's interaction with the user interface thereof may be a false negative—i.e. a response to a prompt that does not automatically result in the user taking an action (such as muting a notification, marking a task as completed, etc.). These and other inefficiencies are learned by the machine learning module, and appropriate user interface modifications are made. On the other hand, overly frequent monitoring and updates may cause difficulties during usage, leading to lack of use, negative results, as well as poor resource consumption and inefficiencies in the network, application server, and wireless devices connected thereto. In another exemplary embodiment, in the case of technical support, the additional prompt may comprise an alert or instruction to monitor the user interface for a specific instruction or activity, or an instruction to perform a task, such as switching on or off a specific electronic device, or executing a command. In some cases, the alert may further be generated at the application server or at another user interface used by a specialist, such as a technical support agent or a healthcare provider.

Figure 4:
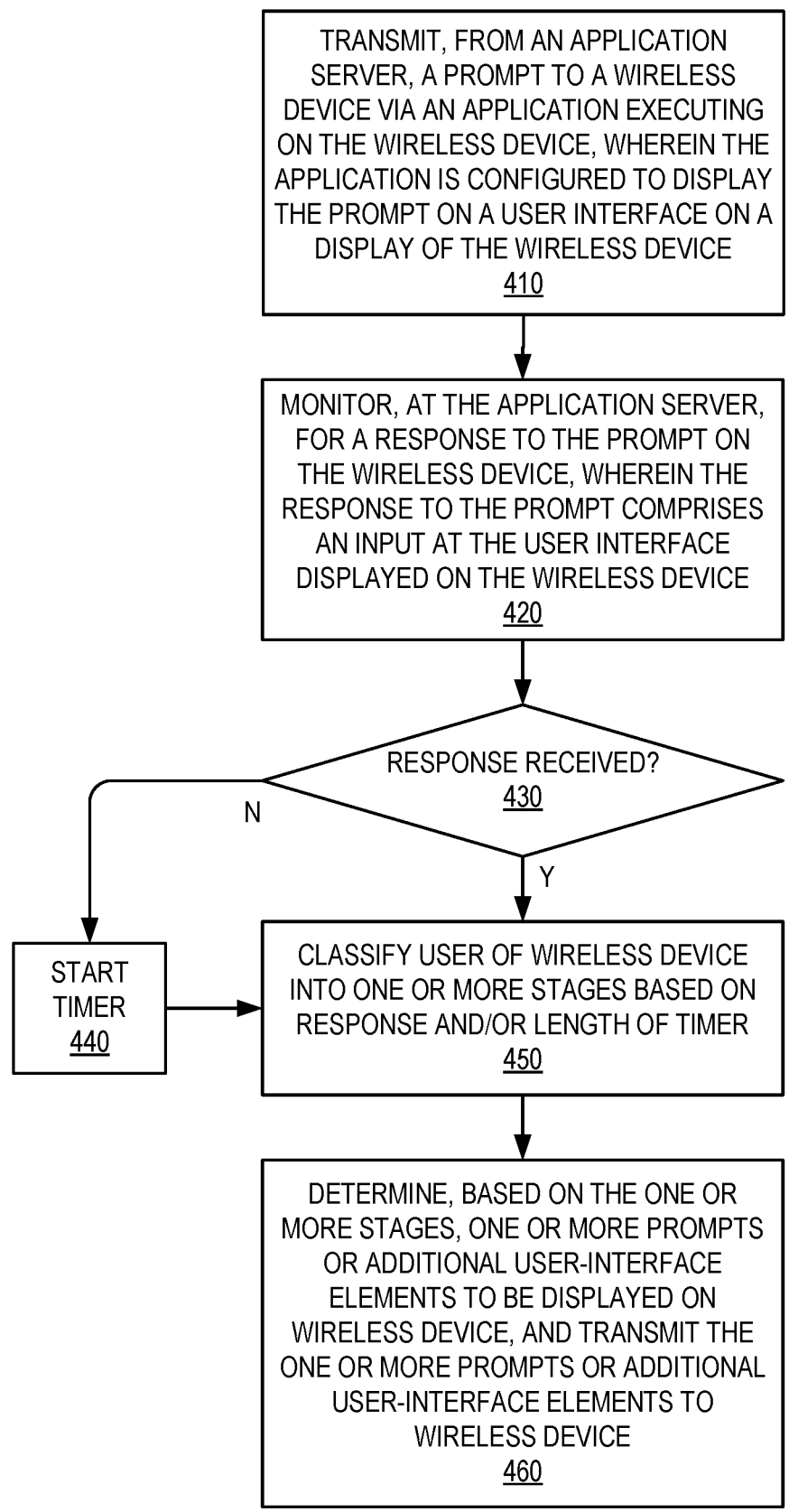
FIG. 4 depicts another exemplary method for personalizing applications based on usage.

FIG. 4 depicts another exemplary method for personalizing applications based on usage. The exemplary method of FIG. 4 may be implemented using components similar to those depicted in system 100, such as application server 104. Although FIG. 4 depicts steps performed in a particular order for purposes of illustration and discussion, the operations discussed herein are not limited to any particular order or arrangement. One skilled in the art, using the disclosures provided herein, will appreciate that various features described herein can be omitted, rearranged, combined, and/or adapted in various ways.

At 410, an application server transmits a prompt to a wireless device via an application executing or being executed on a wireless device. The application is configured to display the prompt on a user interface on a display of the wireless device. For example, the user interface displayed by the application comprises one or more user-interface elements with which a user of the wireless device can interact. The prompt may be one of these user-interface elements. Additional user-interface elements are described further herein and with reference to FIGS. 5-8.

At 420, a response to the prompt is monitored by the application server. The response to the prompt may be one of a plurality of user inputs as the user interacts with the one or more user-interface elements displayed on the user interface presented on the wireless device. Thus, monitoring the usage of the application may comprise one or more of detecting a first input to the prompt, measuring a time of the first input, measuring a length of the first input, determining a type of the first input, determining a frequency of responses to the prompt, or determining that there is no input. The type of first input may comprise one or more of a keypress, a button, an alphanumeric string, or a selection from a list.

For example, at 430 and 440, a time to respond is monitored. If a response is not received right away, a timer may be started. Alternatively, the timer may be started as soon as the prompt is displayed. In either case, the timer provides additional information as to the user's interaction with the prompt. Thus, at 450, the user is classified into one or more stages based on any received response as well as the time taken to respond. In other words, the one or more stages in which the user may be classified based, in part, on the usage of the application. The one or more stages may be related to a proficiency level, an interest level, a behavioral level, or any other classification based on the type of application or the requirements of an operator of the application server. Each level may comprise a value on a scale from a minimum value to a maximum value. For example, a user proficiency of the application may range from complete beginner to software professional, or generally be ranked based on expertise or skill level. The classification may further be based on an initial interaction of the application. The initial interaction is programmed by the creator of the application, and includes a survey of questions (or prompts) for the user of the application. Based on the user input during the initial interaction, a preliminary determination may be made of a user's stage (or any other type of category). These operations may be performed using machine learning, as further described herein. Generally, a machine learning algorithm may be trained for a period of time, either by the operator of the application server, or by monitoring the usage of the application for a specified time period or usage threshold.

At 460, the one or more additional prompts may be determined based on the classification of the user. The trained machine learning algorithm may be used to select the additional prompts based on a combination of the classification of the user and/or the interaction with the application. In an exemplary embodiment, in additional to the training stage of the machine learning algorithm, the selection or determination of the additional user-interface elements by the machine learning algorithm may be invoked upon a total number of inputs meeting a threshold. The one or more additional user-interface elements are transmitted to the wireless device, enabling the application to display the one or more user-interface elements on a user interface presented on the wireless device. In other words, an updated interface comprising any combination of user-interface elements is customized to the user of the wireless device, enabling the user to more effectively interact with the user-interface elements presented thereon.

Further, this method may be performed iteratively and in real-time, such that as the interaction or usage of the application changes over time, user interfaces are dynamically modified via real-time updating of user-interface elements. For example, the user may need to be re-classified based on different usage or patterns of interaction with additional user-interface elements. Thus, additional training, learning, monitoring, and/or classification operations may be performed at various frequencies, or in real-time. An optimal frequency may be determined based on a balance of user interface modifications and network resources. Results may be monitored in the form of changing behavior or interaction patterns, and poor or negative results may be caused by an infrequency monitoring. In one exemplary embodiment, a health monitoring and/or recommendation providing application may determine that a user's interaction with the user interface thereof may be a false negative—i.e. a response to a prompt that does not automatically result in the user taking an action (such as muting a notification, marking a task as completed, etc.). These and other inefficiencies are learned by the machine learning module, and appropriate user interface modifications are made. On the other hand, overly frequent monitoring and updates may cause difficulties during usage, leading to lack of use, negative results, as well as poor resource consumption and inefficiencies in the network, application server, and wireless devices connected thereto.

Figure 5A:
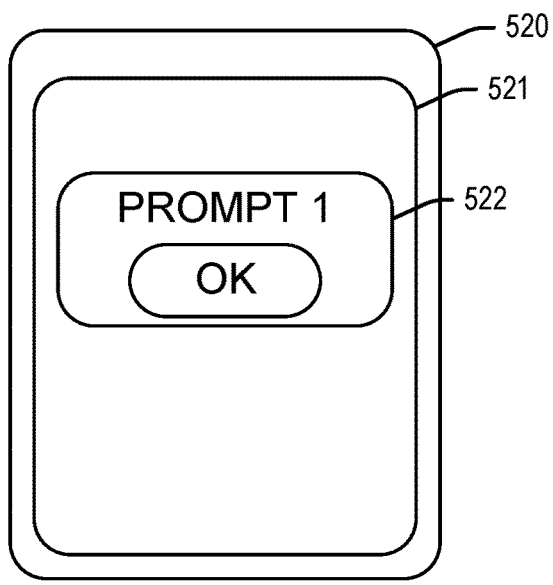
FIGS. 5A-5C depict a first user-interface element displayed on a wireless device, the first user-interface element being modified or selected based on an interaction of a user of the wireless device with the first user-interface element.
Figure 5B:
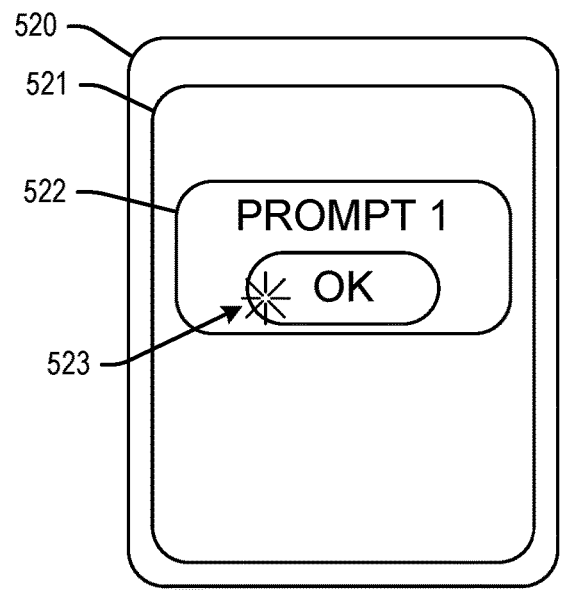
Figure 5C:
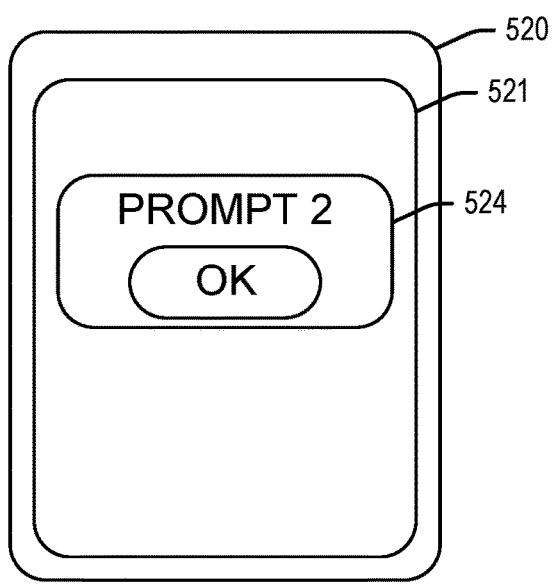

FIGS. 5A-5C depict a wireless device 520 having a display 521 which illustrates at least a first user-interface element 522. With reference to FIG. 5A, user-interface element 522 may comprise a prompt displayed on a user interface that is presented by an application being executed on wireless device 520. With reference to FIG. 5B, monitoring the usage of the application comprises at least detecting a first input 523 to the prompt. The input may comprise, for example, a click or activation of a button within prompt 522. Further, monitoring the input may comprise measuring a time it takes between presenting prompt 522 and input 523, measuring a length of input 523, determining a frequency of input 523 in combination with other responses, or determining that there is no input. Further, a user of wireless device 520 may be classified into one or more stages based on the monitoring. Thus, with reference to FIG. 5C, one or more additional prompts 524 may be determined based on the monitoring, and presented on display 521 of wireless device 520. Additional prompt 520 may be determined based on a combination of the classification of the user and/or the interaction with previous prompts 522, and the selection or determination of additional prompt 524 may be invoked upon a total number of inputs meeting a threshold. Thus, an updated interface comprising any combination of user-interface elements is customized to the user of the wireless device, enabling the user to more effectively interact with the user-interface elements presented thereon.

Figure 6A:
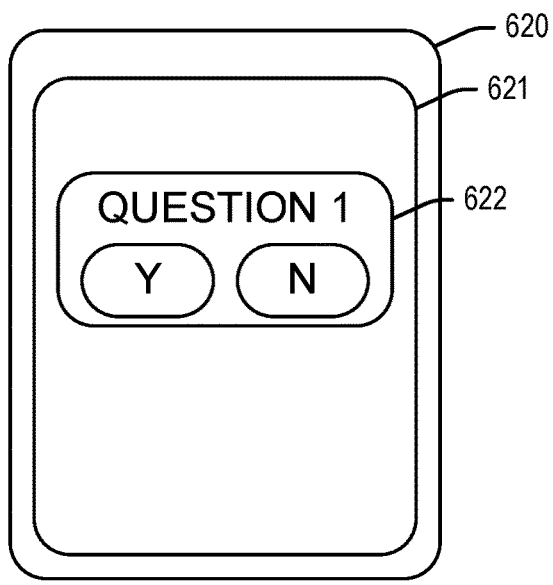
FIGS. 6A-6C depict a second user-interface element displayed on a wireless device, the second user-interface element being modified or selected based on an interaction of a user of the wireless device with the second user-interface element.
Figure 6B:
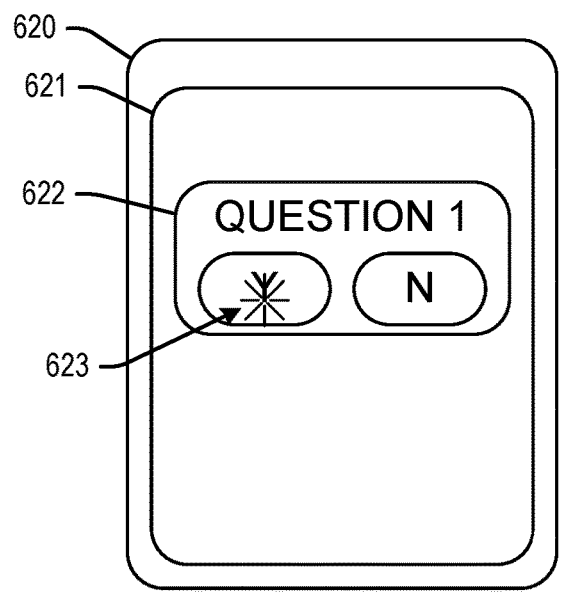
Figure 6C:
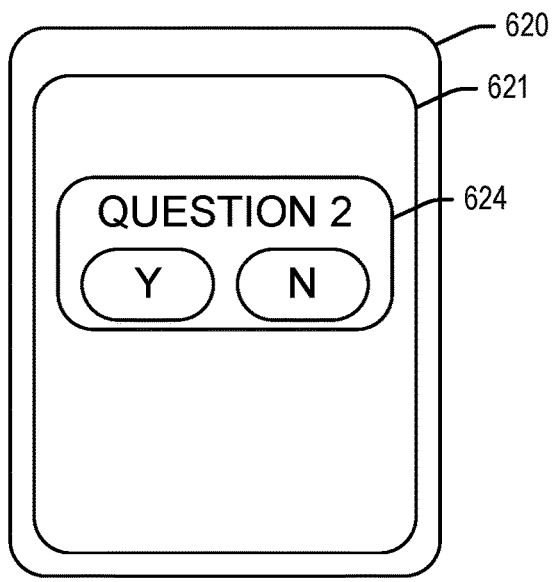

FIGS. 6A-6C depict a wireless device 620 having a display 621 which illustrates at least a first user-interface element 622. With reference to FIG. 6A, user-interface element 622 may comprise a question displayed on a user interface that is presented by an application being executed on wireless device 620. With reference to FIG. 6B, monitoring the usage of the application comprises at least detecting a first input 623 to the question 622. The input may comprise, for example, a click or activation of a button within question 622. Further, monitoring the input may comprise measuring a time it takes between presenting question 622 and input 623, measuring a length of input 623, determining a frequency of input 623 in combination with other responses, or determining that there is no input. Further, a user of wireless device 620 may be classified into one or more stages based on the monitoring. Thus, with reference to FIG. 6C, one or more additional questions 624 may be determined based on the monitoring, and presented on display 621 of wireless device 620. Additional question 620 may be determined based on a combination of the classification of the user and/or the interaction with previous questions 622, and the selection or determination of additional questions 624 may be invoked upon a total number of inputs meeting a threshold. Thus, an updated interface comprising any combination of user-interface elements is customized to the user of the wireless device, enabling the user to more effectively interact with the user-interface elements presented thereon.

Figure 7A:
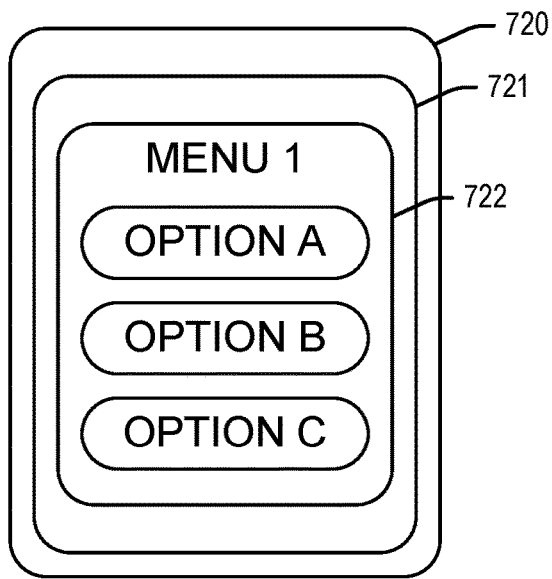
FIGS. 7A-7C depict a third user-interface element displayed on a wireless device, the third user-interface element being modified or selected based on an interaction of a user of the wireless device with the third user-interface element.
Figure 7B:
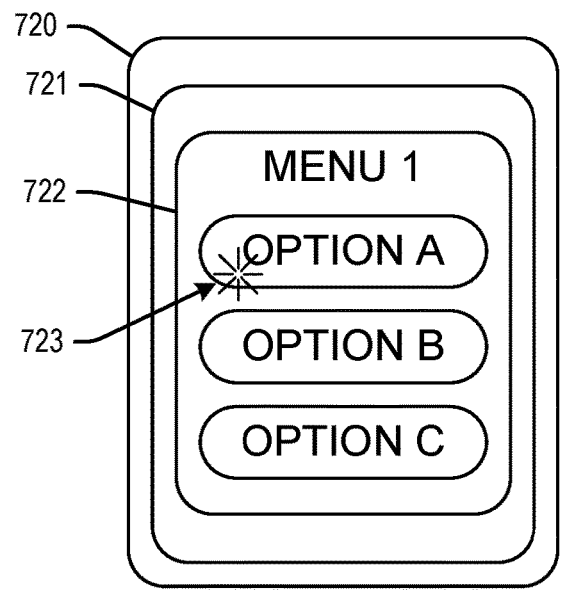
Figure 7C:
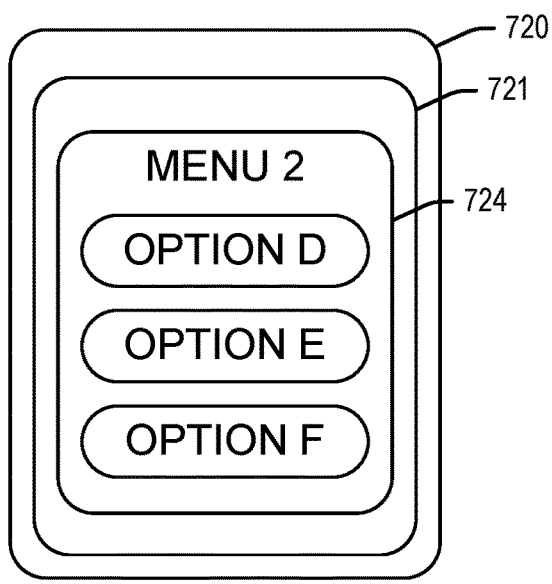

FIGS. 7A-7C depict a wireless device 720 having a display 721 which illustrates at least a first user-interface element 722. With reference to FIG. 7A, user-interface element 722 may comprise a menu displayed on a user interface that is presented by an application being executed on wireless device 720. With reference to FIG. 7B, monitoring the usage of the application comprises at least detecting a first input 723 to the menu 722. The input may comprise, for example, a selection of an option or button presented within menu 722. Further, monitoring the input may comprise measuring a time it takes between presenting menu 722 and input 723, measuring a length of input 723, determining a frequency of input 723 in combination with other responses, or determining that there is no input. Further, a user of wireless device 720 may be classified into one or more stages based on the monitoring. Thus, with reference to FIG. 7C, one or more additional menus 724 may be determined based on the monitoring, and presented on display 721 of wireless device 720. Additional menu 720 (and options presented therein) may be determined based on a combination of the classification of the user and/or the interaction with previous menus 722, and the selection or determination of additional menu 724 may be invoked upon a total number of inputs meeting a threshold. Thus, an updated interface comprising any combination of user-interface elements is customized to the user of the wireless device, enabling the user to more effectively interact with the user-interface elements presented thereon.

Figure 8A:
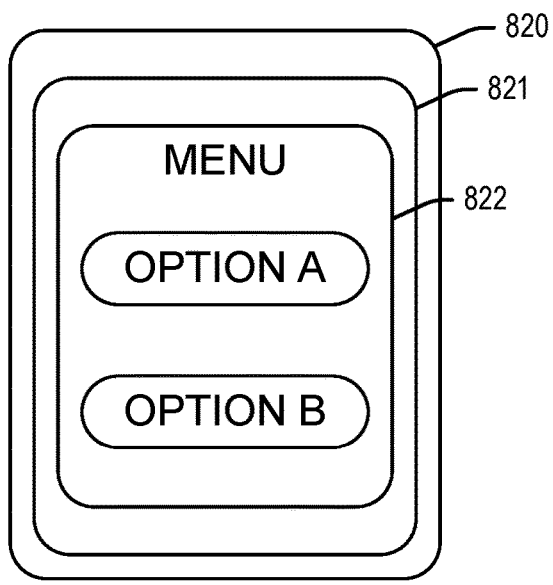
FIGS. 8A-8C depict a fourth user-interface element displayed on a wireless device, the fourth user-interface element being modified or selected based on an interaction of a user of the wireless device with the fourth user-interface element.
Figure 8B:
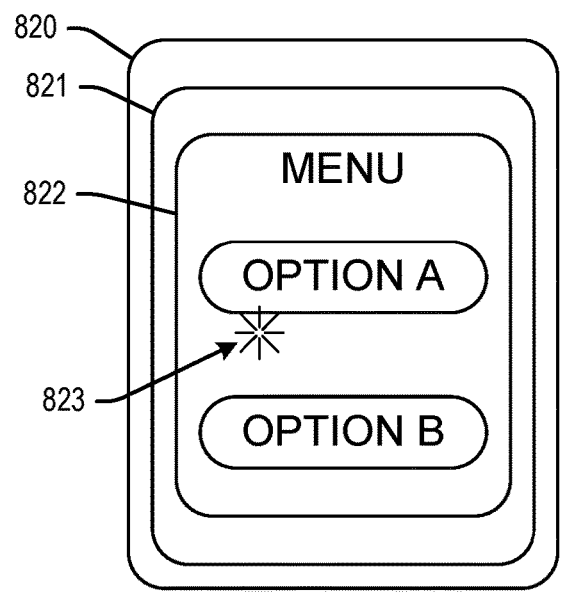
Figure 8C:
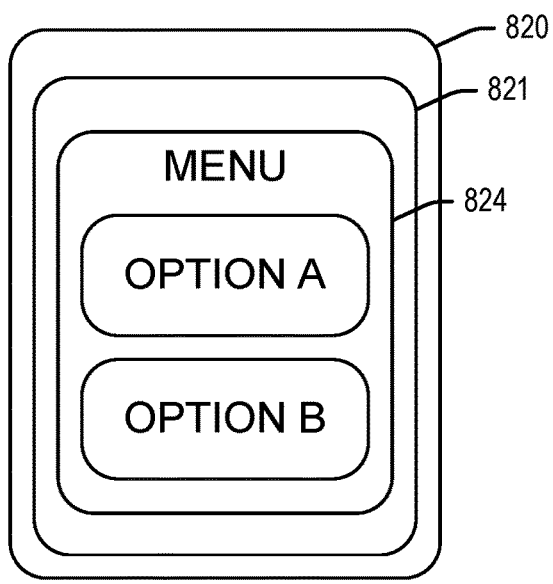

FIGS. 8A-8C depict a wireless device 820 having a display 821 which illustrates at least a first user-interface element 822. This embodiment illustrates modification of a user-interface element (that is, menu 821) to show larger choices based on mistaken or incorrect inputs 823. With reference to FIG. 8A, user-interface element 822 may comprise a menu displayed on a user interface that is presented by an application being executed on wireless device 820. With reference to FIG. 8B, monitoring the usage of the application comprises detecting an incorrect input 823 to the menu 822. The incorrect input may comprise, for example, an activation of an input device (such as touchscreen 821) at a location that does not match with any option or button presented within menu 822. Further, monitoring the incorrect input may comprise determining that a frequency of input 823 in combination with other incorrect or erroneous responses is higher than a threshold. Upon determining an incorrect input (or threshold amount thereof), a user of wireless device 820 may be classified into one or more stages associated with incorrect inputs, such as somebody with limited manual dexterity, or any other inability to navigate the user interface. Thus, with reference to FIG. 8C, a modified menu 824 may be determined, and presented on display 821 of wireless device 820. In this embodiment, options presented on menu 824 may be increased in size, based on a combination of the classification of the user and/or the interaction with previous menu 822. Thus, an updated interface comprising more navigable user-interface elements is customized to the user of the wireless device, enabling the user to more effectively interact with the user-interface elements presented thereon.

In further exemplary embodiments, a medical sensor may be coupled to wireless device (as illustrated in FIG. 1). In these embodiments, sensor data from one or more medical sensors may be used to determine the one or more additional prompts or user-interface elements based on a combination of the usage data and the sensor data. Further, commands may be transmitted to one or more of the plurality of sensors based on the sensor data and the usage of the application. The commands may comprise a calibration command to calibrate the at least one sensor. The commands may further comprise a measurement command to the at least one sensor to perform a measurement. The plurality of sensors may comprise health sensors.

As further mentioned above, a machine learning algorithm may be used to monitor usage of an application and determine updates and/or modifications to the user interface thereof based on said usage. In an exemplary embodiment, dynamic behavior classification module may be combined with a crowdsourcing approach to obtain usage patterns, and an underlying probability distribution of a group or population of users may be determined. For example, a method that uses the learnt probability distribution to classify a user displaying a particular usage pattern based on the experience with other users who displayed similar usage patterns. Further, as described below, a modified Q-learning algorithm may provide dynamic behavior classification even in the absence of labelled training data that maps usage patterns to behavioral stages. Further, the modified Q-learning algorithm may learn the mapping from usage patterns to behavioral stages purely on the basis of user feedback. Such learned mapping can serve as a reliable data source for applying supervised learning techniques for behaviour classification into various stages based on application usage data.

In an exemplary embodiment, application usage data is monitored for the purposes of predicting a user's completion of a goal, such as a learning, health, or other goal, and stages such as adding a goal, completing a goal, etc. may be determined based on reminders, frequency of accessing the app, frequency of reading the content, etc. Such behavior classification is a self-learning stage prediction module to dynamically assess the user present stage of behavior change, by integrating three streams of the data (I) subtle user's feedbacks on recommendations, (II) intake survey module and (III) the application usage pattern. A machine learning module may continuously learn & monitor the behavior stages through these streams of the data. For example, while a user interacts with an application, a module coupled to the application (either local to the wireless device, or as part of application server) may collect and record information about a usage pattern like the number of goals added by a user, the number of goals completed, the number of medications that she has added to the application, the number of reminders she has set, the number of times she has taken the survey, the course recommendations that she has responded to, the number of days since she was last active on the application etc. Such a front-end module may transmit this usage data to a machine learning algorithm (stored on, for example, the application server) which converts the information into a vector of features called as the user's application usage pattern.

In an exemplary embodiment, the dynamics of user stage of behavior may be based on a Markov Decision Process. This may be divided into states, i.e. classification of various application usage patterns into one or more of a category or "bucket", actions, i.e. predictions or determinations of stage of a user, and transition, i.e. changes in the user's application usage pattern (setting more reminders, adhering to goals set, using the application more frequently or less frequently, etc.). The Markov Decision Process can be monitored by the application server on a periodic basis, such as daily or weekly, and any detected change corresponds to a transition from a particular usage state to another. Finally, a reward may be considered as feedback given by the user to the recommendation shown to her. For example, reward may be modeled as an explicit feedback that the user gives to the application. It is possible to consider a case where this reward could be implicitly collected by alternative mechanisms as well.

The underlying dynamics of this process is such that if the user is shown the right recommendations, she will eventually transition to a "maintenance state" and stay in it as often as possible. This is a reasonable assumption to make as without such an assumption, any learning is not possible. The objective is then to find the optimal policy which is a mapping from states to actions. In other words, the goal is to find the right action given a state of the application (or usage pattern) which maximizes long term expected reward.

In an exemplary embodiment, a Q-value denoted by Q(s,a) for each state-action pair is defined as follows:

$$Q(s,a) = \text{expected reward if performance of action } a \text{ at state } s.$$

If Q(s,a) is computer for each state-action pair, the problem of finding the optimal policy will reduce to choosing the action a that has the maximum Q(s,a) given a state s. To compute the values Q(s,a), a modified Q learning algorithm is used. Q learning is an algorithm in reinforcement learning that allows the agent to learn the utility values for every state-action pair known as Q-values. Initially the Q-values for all state-action pairs may be assumed to be zero. The agent takes an action 'a' in state 's' and updates the Q-value for the corresponding state-action pair based on the reward received. The general Q-learning algorithm starts off with initial guesses Q (s, a) for all Q-values. These values are gradually updated based on the following update rules for a deterministic world and a probabilistic world, as further illustrated below:

Deterministic World:
In state s, do a, go to s', get reward r:

$$Q(s,a) \leftarrow r + \gamma \max a'Q(s',a')$$

Where γ is the discount factor.
Probabilistic World:
On the t'th update of Q (s, a):

$$Q(s,a) \leftarrow (1-\alpha t)Q(s,a) + \alpha t[r + \gamma \max a'Q(s',a')]$$

where αt is the learning rate.

The following assumptions are made for the Markov Decision Process, and then modified Q learning algorithm is defined based on these assumptions:

1. The Q-values for a state-action pair depend only on the immediate reward and are independent of the next state. Hence the Q-value update rule case will look as follows: On the t'th update of Q (s, a):

$$Q(s,a) \leftarrow (1-\alpha t)Q(s,a) + \alpha t(r)$$

Where α=1/t

2. The optimal policy is such that the user will eventually transition to a state that corresponds to the maintenance TTM stage of behavior.

In an exemplary embodiment, this Q-learning technique is modified for solving the problem of predicting the user stage of behavior. The modified algorithm is different from the traditional Q learning approach in two ways. The first difference lies in the source of reward. While in traditional Q-learning the immediate reward for a particular state-action pair is a fixed integer, the reward in the exemplary embodiment comes from the user feedback which is not deterministic in nature. The second difference lies in the Q-value update rule as discussed earlier. The user feedback may comprise specific prompts designed to include specific usage information, such as user preferences, quality of experience, and other feedback.

A common Q-table may be maintained for all users of an application, and the Q-value updated by taking a running average of the user feedback/reward and the previous Q-value (which, in turn, comprises an average feedback based on the predictions made so far). Consequently the Q-value Q(s,a) captures the average feedback given by the users so far for choosing action a in state s. In the process of making predictions and updating the Q-values, the Q-table can converge to the underlying probability distribution of the population across different stages for a given state. After convergence the predictions made by the algorithm will be as good as the optimal algorithm that already knows the underlying probability distribution. Initially the Q-values for all state action pairs are initialized to zero and saved in a data structure known as the Q-table. A common Q-table is maintained for all the users of the application. Given that the user is in some state 's', this module predicts the stage of behavior based on the application usage data and/or patterns, as follows 1) Choose a random number between [0,1]. If random number <epsilon, 2) Choose a stage randomly. 3) Else, predict the stage with the highest Q-value according to the experience saved in the Q-table (that is, the stage that the q average population suggested through its feedback). 4) Show recommendation based on predicted stage. 5) Update the Q-values based on the user feedback by taking a running average. Here epsilon is a parameter that controls the exploration and exploitation of the state space. Epsilon is initialized with a high value of 0.9 so as to increase the randomness in the predictions during the initial learning phase of the application. Gradually as the learning proceed, the epsilon is lowered with time so that the application does not waste much time in exploring and starts exploiting the experience gained so far.

The final prediction combines both the state predicted by the intake survey and that predicted by the app usage based modified Q-learning algorithm.

$$\text{Final predicted stage} = w^* \text{intake\_survey\_prediction} + (1-w)^* \text{app\_usage\_prediction}$$

The final prediction comprises a weighted average of the predictions made by the intake survey and the app usage data. Here, w is the weight given to the intake survey prediction, the weight given to the intake survey will reduce with time and the activeness of the user. After 30 days, the intake survey will expire and predictions will be based purely on the basis of app usage data. Because of the weighted average formula, the predicted user stage at any time will always lie between the initial user stage at the time of the intake survey and the stage of behavior of the average population. Thus, both crowdsourcing and a user's personal profile are used in making predictions about the user's behavior.

The disclosed usage data may further be utilized to identify a user's preference and liking towards types of content based on subtle patterns underlying the interaction of the user interface presented on a device. For example, additional user interface elements may be presented in a form that has the highest likelihood of influencing the user. The likeliness of influencing a user may be estimated given a persuasion strategy based on user feedback. A threshold number of times that an additional set of user-interface elements needs to be presented or interacted with may attempted prior to categorizing a user or changing or modifying the user-interface elements, while minimizing inefficient data transmittal across the network and to/from the application server and wireless device.

For example, upon determining the stage of the (based, for example, on application usage patterns explained above), user-interface elements relevant to said stage are displayed on a user interface of the wireless device. Certain user-interface elements are targeted for a combination of a current state for a user and specific to that user irrelevant of state. For example, a user may be proficient at using an application that displays large prompts, whereas another user needs large prompts as well as a simplified hierarchical structure. Further, seemingly unrelated usage patterns may correlate to specific user-interface elements, such as language choices, etc.

Thus, the subject disclosure proposes systems and methods to make usage and interactions with networked applications more efficient based on identification of usage patterns and adjustments to user-interfaces and communications between application servers and devices connected thereto. Direct and subtle interactions are monitored and used to dynamically generate personalized user-interface elements such as prompts, menus, menu structures, display characteristics (like font size, icon size, etc.), among others. These determinations are enabled by classifying usage into stages of behavior, and factoring in users' responses towards different persuasion strategies. Machine learning tools are used to generate a library of user-interface elements that are associated with the stages, and personalized for different combination of usage patterns. The disclosed embodiments may be integrated into various network systems that dynamically changes content according to changing user behavior, such as health, application development, network topology, and other improvements to technology.

The above description and associated figures teach the best mode of the invention. The following claims specify the scope of the invention. Note that some aspects of the best mode may not fall within the scope of the invention as specified by the claims. Those skilled in the art will appreciate that the features described above can be combined in various ways to form multiple variations of the invention. As a result, the invention is not limited to the specific embodiments described above, but only by the following claims and their equivalents.

What is claimed is:

1. A system for personalizing an application, the system comprising:
    an application server for hosting an application that is executed on a wireless device; and
    a processor coupled to the application server, the processor being configured to perform operations comprising:
        transmitting, via the application, a first user interface element to the wireless device, wherein the first user interface element comprises at least one of a prompt, a question, and a menu for an input;
        displaying the first user interface element on the wireless device;
        monitoring a usage of the first user interface element, wherein the monitoring comprises monitoring an interaction between a user of the application and the first user interface element, and wherein the monitoring further comprises detecting a first input to the prompt, measuring a time of the first input, measuring a length of the first input, determining a type of the first input, or determining that there is no input;
        initiating a timer as soon as the first user interface element is displayed;
        classifying said user into one or more stages based on a first input provided to the first user interface element and an elapsed time measured by the timer for the first input, wherein the one or more stages are related to at least one of a proficiency level, an interest level, and a behavioral level, and wherein a level of each stage ranges from a minimum value to a maximum value;
        determining, using a trained machine learning algorithm, one or more additional user-interface elements, based on both the monitoring and the classifying;
        transmitting the one or more additional user-interface elements to the wireless device; and
        displaying the one or more additional user interface elements on the wireless device,
    wherein the one or more additional user interfaces are dynamically modified via real-time updating of user-interface elements,
    wherein the machine learning algorithm is a modified Q-learning algorithm comprising a plurality of Q-value (s, a) state-action pairs, and
    wherein a reward for each Q-value (s, a) state-action pair is based on user feedback for choosing action a in state s, and wherein the action corresponds to classifying said user into a stage and the state corresponds to the first user interface element.

2. The system of claim 1, wherein the type of the first input comprises one or more of a keypress, a button, an alphanumeric string, or a selection from a list.

3. The system of claim 1, wherein the one or more stages comprise one or more levels on a scale.

4. The system of claim 1, wherein the one or more additional user-interface elements are determined based on the one or more stages.

5. The system of claim 4, wherein the stages are arranged in a hierarchical order, and the one or more additional user-interface elements are grouped in a corresponding hierarchical order.

6. The system of claim 4, wherein the one or more additional user-interface elements comprise one or more of a second prompt, a notifier, a question, or an instruction.

7. The system of claim 1, wherein the machine learning algorithm is invoked upon a number of inputs meeting a threshold, the threshold including the first input.

8. The system of claim 1, further comprising a medical device in communication with the wireless device.

9. The system of claim 8, wherein operations further comprise:
    receiving sensor data from a sensor coupled to the medical device; and determining the one or more additional user-interface elements based on a combination of the usage of the application and the sensor data.

10. The system of claim 9, wherein the operations further comprise transmitting commands to the medical device based on the sensor data and the usage of the application, wherein the commands comprise one or more of a calibration command to calibrate the sensor, a measurement command to the medical device to perform a measurement, an alert command to the medical device to generate an alert, or an action command to administer a treatment.

11. The system of claim 10, wherein transmitting commands to the medical device is performed by the application server via the wireless device.

12. A method for personalizing an application, the method comprising:
    transmitting, by an application server, a first user interface to a wireless device via an application hosted on the application server and executed on the wireless device, wherein the first user interface element comprises at least one of a prompt, a question, and a menu for an input;
    displaying the first user interface element on the wireless device;
    monitoring, by the application server, a usage of the first user interface, wherein the monitoring comprises monitoring an interaction between a user of the application and the first user interface, and wherein the monitoring further comprises detecting a first input to the prompt, measuring a time of the first input, measuring a length of the first input, determining a type of the first input, or determining that there is no input;
    initiating a timer as soon as the first user interface element is displayed;
    classifying said user into one or more stages based on input provided to the first user interface element and an elapsed time measured by the timer for the first input, wherein the one or more stages are related to at least one of a proficiency level, an interest level, and a behavioral level, and wherein a level of each stage ranges from a minimum value to a maximum value;
    determining, using a trained machine learning algorithm, a second user interface based on both the monitoring and the classifying;
    transmitting, by the application server, the second user interface to the wireless device via the application; and displaying the second user interface on the wireless device, wherein the second user interface is dynamically modified via real-time updating of user-interface elements, wherein the machine learning algorithm is a modified Q-learning algorithm comprising a plurality of Q-value (s, a) state-action pairs, and wherein a reward for each Q-value (s, a) state-action pair is based on user feedback for choosing action a in state s, and wherein the action corresponds to classifying said user into a stage and the state corresponds to the first user interface element.

13. The method of claim 12, wherein the first user interface comprises a first plurality of user-interface elements, and the second user interface comprises a second plurality of user-interface elements.

14. The method of claim 12, further comprising determining the second plurality of user-interface elements of the second user interface based in part on the one or more stages.

15. The method of claim 12, further comprising determining the second plurality of user-interface elements of the second user interface based on a combination of the usage and data received from a sensor in communication with the wireless device.

16. The method of claim 15, wherein:
the sensor further comprises a medical device,
the data comprises a physiological measurement, and
the method further comprises determining the second plurality of user-interface elements based in part on the physiological measurement.

* * * * *